United States Patent [19]

Gutnick et al.

[11] Patent Number: 4,883,757
[45] Date of Patent: Nov. 28, 1989

[54] BIOEMULSIFIER PRODUCTION BY ACINETOBACTER CALCOACETICUS STRAINS

[75] Inventors: David L. Gutnick, Moshav Sdei Hemed, Israel; Eirik Nestaas, Chestnut Hill, Mass.; Eugene Rosenberg, Raanana; Nechemia Sar, Holon, both of Israel

[73] Assignee: Petroleum Fermentations N.V., Curacao, Netherlands Antilles

[21] Appl. No.: 129,389

[22] Filed: Nov. 24, 1987

Related U.S. Application Data

[63] Continuation of Ser. No. 676,916, Nov. 30, 1984, abandoned.

[51] Int. Cl.$^4$ ............... C12N 1/20; C12R 1/01; B01F 17/00
[52] U.S. Cl. ............... 435/252.1; 435/253.6; 435/822; 252/351
[58] Field of Search ............... 435/99, 101, 200, 253, 435/259, 822, 253.6, 252.1; 252/351, 356

[56] References Cited

U.S. PATENT DOCUMENTS 3,941,692  3/1976  Gutnick et al. ............... 210/11
3,997,398  12/1976  Zajic et al. ............... 195/28 R
4,230,801  10/1980  Gutnick et al. ............... 435/101
4,234,689  11/1980  Gutnick et al. ............... 435/101
4,392,892  7/1983  Wagner et al. ............... 134/25.1
4,395,354  7/1983  Gutnick et al. ............... 252/356

OTHER PUBLICATIONS

Bauman, J. Bacteriol. 96:34, (1968).
Cooper and Paddock, Appl. Environ. Microbiol. 47:173, (1984).
Hisatsuka et al., Agric. Biol. Chem. 35:686, (1971).
Holdom et al., J. Appl. Bacteriol. 32:448, (1969).
Iguchi et al., Agric. Biol. Chem. 33:1657, (1969).
Itoh et al., Agric. Biol. Chem. 36:2233, (1971).
Kaplan and Rosenberg, Appl. Environ. Microbiol. 44:1335, (1982).
Rosenberg et al., Appl. Environ. Microbiol. 37:402, (1979).
Sar and Rosenberg, Current Microbiol. 9:309, (1983).
Suzuki et al., Agric. Biol. Chem. 33:1619, (1969).
Zajic et al., Crit. Rev. Microbiol. 5:39, (1976).
Zajic et al., Chemosphere 1:51, (1972).
Zajic et al., Biotechnol. Bioeng. 14:331, (1972).
Zajic et al., Dev. Ind. Microbiol. 12:87, (1971).

Primary Examiner—Elizabeth C. Weimar
Attorney, Agent, or Firm—Pennie & Edmonds

[57] ABSTRACT

Methods and compositions are provided for the preparation and use of new nondialyzable, interfacially-active bioemulsifiers from *Acinetobacter calcoaceticus* strains.

22 Claims, No Drawings

BIOEMULSIFIER PRODUCTION BY ACINETOBACTER CALCOACETICUS STRAINS

This is a continuation of application Ser. No. 676,916, filed Nov. 30, 1984, now abandoned.

TABLE OF CONTENTS

1. Introduction
2. Background of the Invention
3. Summary of the Invention
4. Detailed Description of the Invention
    4.1. Isolation and Characterization of *A. calcoaceticus* Strains
    4.2. Production of Bioemulsifiers by *A. calcoaceticus*
    4.3. Use of the Bioemulsifiers
5. Example: Bioemulsifier Production by *A. calcoaceticus* Strains
    5.1. *A. calcoaceticus* Strains
    5.2. Characterization of the Strains
        5.2.1. Acinetobacter Transformation
        5.2.2. Antibiotic Sensitivity
        5.2.3. Growth on Various Carbon Sources
    5.3. Extracellular Bioemulsifier Production
        5.3.1. Analytical Procedures
        5.3.2. Effect of Various Carbon Sources on Bioemulsifier Production by Some *A. calcoaceticus* Strains
        5.3.3. Production of Bioemulsifiers by the Acinetobacter Strains
    5.4. Effect of Protease Treatment on the Bioemulsifiers
    5.5. Preparation of Technical Grade Bioemulsifiers
    5.6. Additional Preparations of *Acinetobacter calcoaceticus* Bioemulsifiers
6. Deposits of Microorganisms

1. INTRODUCTION

This invention relates to nondialyzable interfacially-active bioemulsifiers produced by strains of *Acinetobacter calcoaceticus*. These bioemulsifiers differ with respect to the hydrocarbons that they can most effectively emulsify. Some of the bioemulsifiers are more effective when used with straight chain aliphatic compounds, some preferentially emulsify aromatic hydrocarbons and still others display similar efficacy with either of the two broad hydrocarbon classes.

This invention further relates to a general method for the screening of *Acinetobacter calcoaceticus* strains and for the production and use of bioemulsifiers therefrom.

2. BACKGROUND OF THE INVENTION

Many microorganisms can utilize hydrocarbons as a primary carbon source, but potential hydrocarbon substrates are immiscible in water and are often intrinsically viscous. Before such hydrocarbons can be metabolized, they must first be converted to and maintained in a more accessable physical form. Numerous microorganisms accomplish this conversion by producing and exporting surface active and/or emulsifying agents that convert the insoluble, viscous, oil substrates into fine, stable oil-in-water emulsions. The result is a marked increase in the effective hydrocarbon surface area, through which far more effective assimilation and metabolism of the hydrocarbons may occur.

Among the microbes with this ability is *Mycobacterium rhodochrous* NCIB 9005, which Holdom et al. [J. Appl. Bacteriol. 32:448 (1969)] showed produces a nonionic surface active agent during growth on n-decane. Iguchi et al. [Agric. Biol. Chem. 33:1657 (1969)] found that *Candida petrophilium* produced a surface active agent consisting of peptides and fatty acid residues, while Suzuki et al. [Agric. Biol. Chem. 33:1619 (1969)] reported that trehalose lipid appeared in the oil phase of cultures of various Arthrobacter, Brevibacterium, Corynebacterium and Nocardia strains. Wagner has reported the production of trehalose lipids by *Nocardia rhodochrous* and *Mycobacterium phlei* and their use in oil recovery [U.S. Pat. Nos. 4,392,892 and 4,286,660].

*Torulopsis gropengiesseri* was found to produce a sophorose lipid, while rhamnolipids are reported by Hisatsuka et al. [Agric. Biol. Chem. 35:686 (1971)] to have been produced by *Pseudomonas aeruginosa* strain S7B1 and by Itoh et al. [Agric. Biol. Chem. 36:2233 (1971)] to have been produced by another *P. aeruginosa* strain, KY4025. The growth of *Corynebacterium hydrocarboclastus* on kerosene was reported by Zajic and his associates [Dev. Ind. Microbiol. 12:87 (1971); Biotechnol. Bioeng. 14:331 (1972); Chemosphere 1:51 (1972); Crit. Rev. Microbiol. 5:39 (1976); and U.S. Pat. No. 3,997,398] to produce an extracellular heteropolysaccharide which, among other properties, emulsified kerosene, Bunker C fuel oil and other fuel oils.

Gutnick et al. [U.S. Pat. Nos. 3,941,692; 4,230,801; 4,234,689 and 4,395,354] have shown that *Acinetobacter calcoaceticus* ATCC 31012 (RAG-1) produces at least two polyanionic protein-associated lipopolysaccharide biopolymers with strong activity as emulsion stabilizers. These interfacially active agents, collectively called emulsans, encapsulate the bacteria and are also released to the surrounding medium. More recently, Kaplan and Rosenberg [Appl. Environ. Microbiol. 44:1335 (1982)] showed that *A. calcoaceticus* BD-4 and BD-413 produce extracellular polymeric bioemulsifiers. The bioemulsifier from BD-413 contained rhamnose and glucose in a 3:1 molar ratio.

The ability to produce bioemulsifiers extends beyond the bacteria. For example, Cooper and Paddock [Appl. Environ. Microbiol. 47:173 (1984)] have reported that the yeast *Torulopsis bombicola* produces a mixture of glycolipids that act as a biosurfactant. Most of the surfactant is produced in the late exponential phase of growth when the yeast is cultured.

3. SUMMARY OF THE INVENTION

Methods and compositions are provided for the production of a number of bioemulsifiers and emulsion stabilizers from strains of *Acinetobacter calcoaceticus*. These bioemulsifiers are believed to be capsular polymers that are shed into the surrounding medium during the growth of the strains. All of sixteen strains examined produced bioemulsifiers to some degree, suggesting that this ability may be characteristic of all *A. calcoaceticus* strains.

Some of the *A. calcoaceticus* strains examined, designated NS-1, -4, -5, -6 and -7, have been characterized for their antibiotic sensitivities. All of the strains have been characterized for their ability to produce bioemulsifiers under a defined set of culture conditions and for the hydrocarbon specificities of the bioemulsifiers thereby produced.

Bioemulsifiers are described which preferentially emulsify aqueous mixtures containing hexadecane. Others are more effective in the emulsification of a hexadecane/2-methylnaphthalene mixture or of 2-ethylnaphthalene in water. Taken together, the bioemulsifiers of this invention have the ability to emulsify a wide range of hydrocarbons and to stabilize the emulsions once they have been formed.

The bioemulsifiers of this invention may be used as whole broth or total lysates of the *A. calcoaceticus* cultures in which they are produced, as cell-free medium from such cultures, as apo-bioemulsifiers from which associated proteins or polypeptides have been removed, or in a form in which any associated proteins have been enzymatically or chemically denatured or degraded. The bioemulsifiers may also be solvent extracted to remove non-covalently bound lipids, dialyzed to remove salt, or ion-exchanged to replace counterions. They may also be applied as liquid solutions or slurries, or as a dried powder.

4. DETAILED DESCRIPTION OF THE INVENTION

4.1. Isolation and Characterization of *Acinetobacter calcoaceticus* Strains Acinetobacter species are widely distributed in nature. Although they are most commonly found in water, mud and soil, they have also been found in the eye, ear, repiratory tract and vagina of human beings, in tissues and body fluids of other animals and in foods. Given a source of the bacteria, standard microbial isolation procedures may be employed to develop stocks.

The Acinetobacters of the present invention were isolated from water, soil or mud by the method of Bauman [J. Bacteriol. 96:34 (1968)], although numerous other methods that have been described may also be suitable. In the Bauman method, inoculates of soil or water samples are subjected to vigorous shaking in an acetate buffer at pH 6. The effect of this treatment is to enrich the culture with Acinetobacters while at the same time decreasing the relative contribution by Pseudomonads that are also likely to be present in the samples. Samples of the turbid mixed cultures may then be streaked onto agar containing an appropriate minimal medium, for microbial propagation and characterization.

All of the microbial strains of this invention have been classified as *A. calcoaceticus*. All of the cells are gram-negative, oxidase-negative, aerobic, nonmotile coccoid rods. In the past, phenotypic properties have been used to classify bacteria as Acinetobacter. See, e.g., Bauman et al., J. Bacteriol. 95:1520 (1968); Gilardi, J. Microbiol. Serol. 35:421 (1969) and Thornley, J. Gen. Microbiol. 49:211 (1967). In the preferred embodiment of this invention, however, the interspecies transformation method of Juni [J. Bacteriol. 112:917 (1972)] was used instead. This method employs deoxyribonucleic acid from related strains to transform a competent Acinetobacter auxotroph to prototrophy.

The exemplary *A. calcoaceticus* strains of this invention include RAG-1, BD4, 1612, 1935, ATCC 17906, ATCC 17924, H01-N and NS-1 through NS-9. Strain RAG-1 has been described previously by Rosenberg et al. [Appl. Environ. Microbiol. 37:402 (1979)], while strains NS-1 through NS-9 were isolated from fresh environmental samples as described below [Sar and Rosenberg, Current Microbiol. 9:309 (1983)]. The other strains were obtained from various scientific investigators.

4.2. Production of Bioemulsifiers by *Acinetobacter calcoaceticus*

As previously reported, *A. calcoaceticus* RAG-1 (ATCC 31012) produces bioemulsifiers that are collectively known as emulsans [see, e.g., Gutnick et al., U.S. Pat. No. 4,395,354]. More recently, it was found that *A. calcoaceticus* BD-413 also produces a bioemulsifier [Kaplan and Rosenberg, Appl. Environ. Microbiol 44:1335 (1982)]. It is the unexpected discovery of this invention that probably all *A. calcoaceticus* strains produce bioemulsifiers, presumably derived from their polysaccharide and/or lipopolysaccharide capsular layers. This discovery stems from the examination of 16 *A. calcoaceticus* strains for the production of extracellular bioemulsifier activity. All of the strains were positive for such activity.

In the preferred embodiment of this invention the bacterial strains were grown in agar containing minimal salts with one of a variety of utilizable carbon sources. Carbon sources that may support the growth of *A. calcoaceticus* include but are not limited to glucose, arginine, alanine, proline, tryptophan and tyrosine. The exact choice of a carbon source must be determined for each strain, since there is considerable individual variation (see Section 5.2.3).

The preferred medium carbon source for bioemulsifier production is also strain dependent, and it is likely to be different from the carbon source needed for maximal bacterial growth. In the example of this invention 0.2% sodium acetate, 2% hexadecane and 2% ethanol were examined in a minimal salt medium for their ability to support cell growth and bioemulsifier production. Of these compounds ethanol was by far the best, yielding the highest specific activity (bioemulsifier production per unit of dry cell weight) and good cell growth. Other low molecular weight carbon sources might also be employed, but their efficacy would have to be established on a strain-by-strain basis.

In the preferred embodiment of this invention, bioemulsifier production was carried out by applying gyrotory shaking to *A. calcoaceticus* cultures in a minimal salt medium containing two volume percent ethanol. Good yields of bioemulsifiers were obtained from a number of strains in this way, but those skilled in the art are aware of numerous other ways in which production could be achieved. For example, conventional submerged fermentations in stirred tanks can be performed. Another possibility might be the porous support method described by Kim et al. in U.S. Pat. No. 4,384,044. Kim et al. describe the production of a polysaccharide by microorganisims immobilized on porous, particulate inert supports having a specified pore size. The method of Kim et al. might be applicable to the present invention because the Acinetobacter strains produce more bioemulsifier when cultivated through a stationary phase, in addition to the initial rapid growth phase (i.e., product formation is partly non-growth associated).

4.3. USE OF THE BIOEMULSIFIERS

The bioemulsifiers of this invention can emulsify, i.e., form and/or stabilize hydrocarbon-in-water emulsions. The *A. calcoaceticus* strains of the invention, however, produce different bioemulsifiers with different hydrocarbon specificities for emulsification. Therefore, it is best to establish which emulsifier is best for a given hydrocarbon that is to be emulsified through simple testing in which an emulsifier, hydrocarbon and water are shaken together. If the specificity of the emulsifier is correct for the hydrocarbon, a murky "cream" will form that will remain stable over a period of minutes or, preferably, hours. Of course, it would also be possible to use a combination of the emulsifiers, thereby increasing the range of hydrocarbons that could be emulsified.

The bioemusifiers can be used effectively in various states of purity. For example, a culture, i.e., a spent fermentation broth containing an *A. calcoaceticus* strain and producing a desired bioemulsifier could simply be applied directly or lysed and used as the total lysate. Lysing of the cells could be carried out in any of the ways that are well known to those skilled in the art, e.g., by induced autolysis, alternate temperature changes, pH changes, additional chaotropic agents (e.g., urea), sonication, osmotic shock or by the use of enzymatic means or by mechanical grinding or use of a French press.

Alternatively, a more pure bioemulsifier preparation may readily be obtained by removing the medium from the bacterial cells, for example by centrifugation, flocculation and sedimentation, cake filtration or microfiltration. The substantially cell-free fluid will then contain the bioemulsifier, the medium components and other microbial products. If a still more pure preparation is desired, the fluid may be extensively dialyzed, preferably against a low ionic strength buffer, to remove low molecular weight contaminant molecules. The bioemulsifier could be further purified or concentrated from the dialysate by a method such as, e.g., selective precipitation, selective solvent extraction or partitioning or selective adsorption onto a solid adsorbant followed by subsequent elution or extraction. Selective precipitation might be carried out with a quarternary ammonium salt such as ammonium sulfate. It might also be done in a low-temperature bath with an organic solvent such as ethanol or acetone.

As they are produced by the Acinetobacters, the bioemulsifiers are likely to be complexed with various proteins or polypeptides. These proteins or polypeptides may either inhibit or enhance the emulsifying activity of the bioemulsifiers. Where it is desirable to eliminate this potential interference, the proteins or polypeptides may be removed to produce the apo-bioemulsifiers. This could be accomplished by phenol extraction at an elevated temperature as described by Gutnick et al. in U.S. Pat. No. 4,395,354. Alternatively, the proteins or polypeptides can be removed from the bioemulsifiers by treatment with a general protease followed by dialysis to remove the digestion fragments. It may also be desirable to retain proteinaceous materials in the bioemulsifier preparation but in a digested form. Thus protease treatments can be performed for the purpose of degrading associated proteins without their removal from the bioemulsifier preparation. In some instances, it has been observed that these degraded protein fragments enhance emulsification ability. The general protease of *Bacillus subtilis* and trypsin are but two examples of proteases that are suited to this task.

Because of their unique abilities in forming and/or stabilizing hydrocarbon-in-water emulsions, the bioemulsifiers of this invention lend themselves to numerous and diverse applications. The bioemulsifiers of this invention can potentially be used for the same environmental and energy-related purposes as described for the emulsans in U.S. Pat. No. 4,395,354. Other energy-related uses are possible as well. For instance, the Acinetobacter bioemulsifiers described herein may be used to stabilize emulsions of hydrocarbons, including viscous crudes and residuals, for pipelining, shipping and storage purposes. They may also be used to stabilize hydrocarbon-in-water emulsions that can be burned as fuels. Such further energy-related uses have been described in co-pending U.S. patent applications Ser. Nos. 547,892 and 653,808, filed November 2, 1983 and September 24, 1984, respectively. Other uses for the bioemulsifiers of this invention include formulation into cosmetic and/or pharmaceutical preparations for human use such as the bioemulsifier-containing soaps and shampoos described in co-pending U.S. patent application Ser. No. 662,931 filed October 16, 1984. The foregoing U.S. patent and U.S. patent applications are hereby incorporated by reference.

5. EXAMPLE: BIOEMULSIFIER PRODUCTION BY *A. CALCOACETICUS* STRAINS

5.1. *A. calcoaceticus* Strains

*A. calcoaceticus* BD-4, originally isolated by Taylor and Juni, was provided by K. Bryn, as were ATCC strains 17906 and 17924. Strain BD-413 trp E27, a miniencapsulated mutant of BD-4, was from E. Juni. *A. calcoaceticus* H01-N was obtained from W. Finnerty, while M. Rosenberg provided strains 1612 and 1935. Strain RAG-1 (ATCC 31012) has been described previously [Rosenberg et al., Appl. Environ. Microbiol. 37:402 (1979)], and PET-11 is a phage-resistant mutant of RAG-1.

Standard enrichment culture techniques described by Bauman [J. Bacteriol. 96:34 (1968)] were used for the isolation of Acinetobacter strains NS-1 to NS-9. Briefly, samples from water, soil or mud were inoculated into 10-ml aliquots of AC medium (0.2% sodium acetate, 0.2% $KNO_3$, 0.02% $MgSO_4.7H_2O$ and 40 mM $KH_2PO_4$-$Na_2HPO_4$ buffer, pH 6.0) in 25-ml Erlenmeyer flasks and subjected to vigorous aeration in a gyrotory shaker at 30° C. for 48 hours.

After the incubation period, samples of the then turbid cultures were streaked onto 2% agar containing AC medium. After incubation for 48 hours at 30° C., colonies appeared that contained nonmotile, oxidase-negative coccobacilli. [Oxidase activity was measured by the method of Bovre and Henricksesen, J. System. Bacteriol. 26:92 (1976).] These bacteria, considered to be possible Acinetobacter species, were transferred to brain-heart infusion (BHI) agar (Difco Laboratories, Detroit, Michigan).

5.2. CHARACTERIZATION OF THE STRAINS

5.2.1. ACINETOBACTER TRANSFORMATION

All of the microbial strains described herein were confirmed as Acinetobacters by a modification of the method of Juni [J. Bacteriol. 112:917 (1972)]. That method tests the ability of suspected Acinetobacter strains to serve as DNA donors for the transformation of a competent, known auxotrophic Acinetobacter to prototrophy. In the present example, *A. calcoaceticus* BD-413 trp E27, a proven Acinetobacter that is auxotrophic for tryptophan, was used as the recipient strain.

To test a suspected Acinetobacter strain, an overnight culture of the strain in 0.5 ml of brain-heart infusion (BHI) medium (Difco Laboratories, Detroit, Michigan) was mixed with 0.5 ml of 0.2% sodium dodecyl sulfate and incubated for 30 minutes at 60° C. A few drops of chloroform were added, and the mixture was incubated for an additional 30 minutes at 60° C. The lysed cell suspension was then cooled and diluted with an equal volume of water.

Transformation was performed by placing a small amount of strain BD-413 bacterial paste, just visible to the naked eye, on a sector of GM agar [21.8 g $K_2HPO_4.3H_2O$, 7.14 g $KH_2PO_4$, 4.0 g $(NH_4)_2SO_4$ and 0.2 g $MgSO_4.7H_2O$ per liter, pH 7.0, with 2% agar (Difco) and 0.2% D-glucose] supplemented with 1 µg/ml of L-tryptophan. Then, the paste was spread, together with a loopful of the lysed cell suspension, and the culture was incubated for 24 hours at 30° C.

After the incubation, a loopful of the developing colonies that appeared were spread onto GM agar without tryptophan and incubated for 24 hours at 30° C. The presence of confluent growth or many colonies on the minimal glucose agar indicated positive transformation of BD-413 trp E27 to prototrophy and identified the donor strain as an Acinetobacter. All of the strains described herein were positive in the test, while controls without donor DNA or lysates from non-Acinetobacter strains were negative.

5.2.2. ANTIBIOTIC SENSITIVITY

To further characterize some of the Acinetobacters of this invention, strains NS-1, -4, -5, -6 and -7 were examined, along with PET-11, for their sensitivity to a variety of antibiotics. PET-11 is a phage-resistant mutant of RAG-1. Like RAG-1, PET-11 is an *A. calcoaceticus* strain that produces bioemulsifiers called emulsans.

The antibiotic tests were carried out with BBL Sensi-Disc microbial susceptibility test discs [Sensi-Disc is a trademark of BBL Microbiology Systems, Cockeysville, Maryland], essentially in accordance with the manufacturer's protocol.

Uniformly diluted cultures of the strains were streaked over the entire sufaces of 10 cm plates containing 20 ml of nutrient broth yeast extract, and the plates were kept covered at room temperature for from three to fifteen minutes. The various test antibiotic discs were then aseptically distributed over the surfaces of the cultures, and the plates were incubated overnight at 37° C.

After the incubation period, the plates were examined and the diameters of clear zones around the discs indicating cell killing were measured to the nearest millimeter. The data, describing the bacterial strains in terms of resistant, intermediate or sensitive as established by the manufacturer's calibration data, are shown in Table 1. As shown in the Table, the pattern of sensitivity to the various antibiotics varied from strain to strain.

TABLE 1

ANTIBIOTIC SENSITIVITY OF THE *A. CALCOACETICUS* STRAINS

| Antibiotic | Bacterial Strain Sensitivity* | | | | | |
|---|---|---|---|---|---|---|
| | PET-11 | NS-1 | NS-4 | NS-5 | NS-6 | NS-7 |
| Ampicillin | R | S | R | R | R | I |
| Erythromycin | I | S | I | I | I | I |
| Gentamycin | R | S | R | I | S | I |
| Tetracycline | I | I | I | S | I | R |
| Trimethoprim | R | I | R | I | I | S |
| Vancomycin | R | R | R | I | R | I |
| Kanamycin | R | I | I | I | I | I |
| Tobramycin | R | I | R | I | I | I |
| Amikacin | I | R | R | I | R | I |

*R, I, and S means resistant, intermediate and sensitive, respectively

5.2.3. GROWTH ON VARIOUS CARBON SOURCES

Other differences among the *A. calcoaceticus* strains of this invention were revealed in growth studies in which a basic medium was supplemented with various carbon sources.

The strains were plated onto MS agar [21.8 g $K_2HPO_4.3H_2O$, 7.14 g $KH_2PO_4$, 4.0 g $(NH_4)_2SO_4$ and 0.2 g $MgSO_4.7H_2O$, pH 7.0, with 2% agar] containing 0.1% (w/v) glucose, arginine, alanine, proline, tryptophan or tyrosine, and the cultures were examined after 48 hours of incubation at 30° C. The degree of growth was noted by visual inspection and growth indicated as strong, weak or none. The thermal sensitivity of the strains was also determined by testing for growth in BHI agar at 42° C. The data are shown in Table 2.

TABLE 2

GROWTH OF *A CALCOACETICUS* STRAINS ON VARIOUS CARBON SOURCES

| Strain | Growth at 42° C.* | Utilizable Carbon Sources** | | | | | |
|---|---|---|---|---|---|---|---|
| | | Glc | Arg | Ala | Pro | Trp | Tyr |
| RAG-1 | − | − | + | + | + | − | + |
| BD-4 | − | − | + | + | + | + | − |
| 1612 | + | + | + | + | + | + | + |
| 1935 | + | − | + | + | + | + | + |
| HO1-N | − | − | − | + | + | + | + |
| 17924 | − | − | − | + | + | − | ± |
| 17906 | − | − | + | − | + | − | − |
| NS-1 | + | − | + | + | + | − | + |
| NS-2 | + | − | + | + | + | + | + |
| NS-3 | + | − | − | + | + | − | + |
| NS-4 | + | − | + | + | + | − | + |
| NS-5 | + | − | + | − | − | − | + |
| NS-6 | + | + | + | + | + | + | + |
| NS-7 | + | − | − | + | + | − | + |
| NS-8 | + | + | + | + | + | − | + |
| NS-9 | + | − | − | + | + | − | − |

*Growth was examined after 48 hours in BHI agar.
**All carbon sources were added to MS agar to a final connection of 0.1% (w/v). Strong, weak and no growth are indicated by the symbols +, ± and −, respectively.

The data indicate that most of the strains were able to grow at the higher temperature. Of the 16 strains, 4 grew on glucose, 11 on arginine, 14 on alanine, 15 on proline, 7 on tryptophan and 12 on tyrosine as the sole carbon and energy source. Interestingly, all of the strains grew on MS agar supplemented with hexadecane vapors (data not shown).

5.3. EXTRACELLULAR BIOEMULSIFIER PRODUCTION

5.3.1. ANALYTICAL PROCEDURES

The standard emulsification assay of Rosenberg et al. [Appl. Environ. Microbiol. 37:402 (1979)] was used to measure extracellular emulsifying activities. Briefly, 0.1–0.5 ml aliquots of dialyzed extracellular fluids and 0.1 ml of a mixture of hexadecane and 2-methylnaphthalene (equal volumes) were combined with TM buffer (20 mM Tris-HCl with 10 mM $MgSO_4$, pH 7.0) in 100-ml flasks to give a final volume of 7.5 ml. The mixtures were incubated at 30° C. with 160 stroke/min reciprocal shaking for one hour to facilitate emulsion formation. Turbidities were then determined in a Klett-Summerson photometer with a green filter.

Turbidity due to mechanical emulsification was determined in emulsifier-free controls and subtracted from all of the measurements. One unit of emulsifying activity per milliliter is defined as that concentration of activity that produces 100 Klett units in the assay mixture.

In an alternative method, the assay was conducted using 250-ml baffled flasks with a final volume of 15 ml (doubling the volume of all reagents), incubated at 30° C. on a gyrotory shaker at 300 rpm for 30 minutes. Turbidity was measured in a Spectronic 20 spectrophotometer at 660 nm.

To examine hydrocarbon specificity for emulsification, the same procedure was used except that 0.1 ml of hexadecane or 2-ethylnaphthalene was used instead of the hydrocarbon mixture.

In the alternative method, 0.2 ml samples were used, as was a mixture of hexadecane and 2-methylnaphthalene.

For the determination of dry weight, aliquots of resuspended washed cells or of cell-free dialysates were placed in tared aluminum foil cups and dried to constant weight at 80° C.

Protein was determined by the Bio-Rad standard microassay (Bio-Rad Laboratories, Richmond, California) using lysozyme as a reference protein. Carbohydrate content was estimated by the method of Spiro [Methods in Enzymology 8:7 (1966)] by measuring reducing sugar generated by hydrolysis in 2N $H_2SO_4$ for 1 hour at 100° C., with glucose as a standard.

5.3.2. Effect of Various Carbon Sources on Bioemulsifier Production by Some *A. calcoaceticus* Strains To compare the ability of several carbon sources to stimulate bioemulsifier production in a number of the *A. calcoaceticus* strains, inoculates from strains PET-11, NS-1, NS-4, NS-5, NS-6 and NS-7 were grown for 72 hours at 30° C. in 50 ml of medium contained in 250-ml flasks. The basic medium contained 16.9 g/L $K_2HPO_4$, 7.26 g/L $KH_2PO_4$, 4.0 g/L $(NH_4)_2SO_4$ and 0.2 g/L $MgSO_4.7H_2O$. To this medium 0.2% sodium acetate, 2% hexadecane or 2% ethanol was added. The flasks were incubated with gyrotory shaking, and at the end of the 72-hour incubation period, the quantity of cells and the activity of the bioemulsifiers produced was determined as described in the alternative assay method above, with 2-methylnaphthalene, hexadecane and mixtures thereof used as hydrocarbons.

The results are shown in Table 3, in which bioemulsifier specific activity in substantially cell-free supernatant is expressed as a function of EACN value. Standing for equivalent alkane carbon number, EACN reflects the average number of carbon atoms per molecule in the test hydrocarbon mixture. An EACN value of 6 indicates a 70/30 mixture (v/v) of 2-methylnaphthalene/hexadecane, 9 indicates a 50/50 mixture (v/v) of 2-methylnaphthalene/hexadecane, 12 indicates a 25/75 mixture (v/v) of 2-methylnaphthalene/hexadecane and 16 indicates 100% hexadecane. Specific activity is measured as the optical density (O.D.) at 660 nm divided by cell mass.

TABLE 3
PRODUCTION OF BIOEMULSIFIERS IN THE PRESENCE OF VARIOUS CARBON SOURCES

| Strain | Carbon Source | Cell Dry weight (g/l) | Bioemulsifier Specific Activity (O.D.$_{660}$/cell dry weight) for EACN* Value | | | |
|---|---|---|---|---|---|---|
| | | | 6 | 9 | 12 | 16 |
| PET-11 | 0.2% Sodium Acetate | 0.42 | 0.36 | 0.14 | 0.14 | — |
| NS-1 | " | 0.02 | — | — | — | — |
| NS-4 | " | 0.29 | 0.42 | — | — | — |
| NS-5 | " | 0.02 | — | — | — | — |
| NS-6 | " | 0.26 | 0.23 | — | — | — |
| NS-7 | " | 0.15 | — | — | — | — |
| PET-11 | 2% Hexadecane | 4.89 | — | — | — | 0.06 |
| NS-1 | " | 2.14 | — | — | — | — |
| NS-4 | " | 0.73 | — | — | — | 0.04 |
| NS-5 | " | 0.65 | — | — | — | 0.19 |
| NS-6 | " | 4.56 | — | — | — | 0.01 |
| NS-7 | " | 0.39 | — | — | — | — |
| PET-11 | 2% Ethanol | 4.64 | 0.45 | 0.44 | 0.19 | 0.13 |
| NS-1 | " | 5.52 | 0.29 | 0.17 | 0.04 | 0.25 |
| NS-4 | " | 4.26 | 0.08 | 0.08 | 0.06 | 0.03 |
| NS-5 | " | 3.72 | 0.61 | 0.55 | 0.44 | 0.15 |
| NS-6 | " | 4.09 | 0.59 | 0.53 | 0.07 | 0.08 |
| NS-7 | " | 2.60 | 0.58 | 0.78 | 0.07 | 0.02 |

*EACN means equivalent alkane carbon number, and it is a measure of the average carbon atom numbers per molecule in a mixture of aromatic and aliphatic hydrocarbons. A value of 6 indicates a mixture of 70% 2-methylnaphthalene and 30% hexadecane (v/v), 16 indicates all hexadecane, 9 indicates a mixture of 50% 2-methylnaphthalene and 50% hexadecane (v/v) and 12 indicates a mixture of 25% 2-methylnaphthalene and 75% hexadecane (v/v).

As shown in Table 3, on the basis of bioemulsifier specific activity, 2% ethanol was the best carbon source. All of the *A. calcoaceticus* strains examined produced bioemulsifiers that were effective in the emulsification of both hydrocarbons and mixtures of them. The strains differed somewhat in the hydrocarbon specificities of the bioemulsifiers that they produced.

5.3.3. PRODUCTION OF BIOEMULSIFIERS BY THE ACINETOBACTER STRAINS

Because medium containing a low level of ethanol was most effective in stimulating the production of bioemulsifiers of high specific activity in some of the strains, all of the strains were tested in a similar medium. Cultures of the various strains were grown in EMS medium [21.8 g $K_2HPO_4.3 H_2O$, 7.14 g $KH_2PO_4$, 4.0 g $(NH_4)_2SO_4$ and 0.2 g $MgSO_4.7 H_2O$ per liter, pH 7.0, with 2 volume percent ethanol]. The cultures were incubated for 72 hours at 30° C., when the cells and cell-free supernatant dialysate were analyzed as described above. Dialysis was sometimes carried out against distilled water.

TABLE 4
EXTRACELLULAR BIOEMULSIFIER PRODUCTION BY *A. CALCOACETICUS* STRAINS*

| Strain | Cell Yield Dry Weight (mg/ml) | Extracellular Dialysate** | | |
|---|---|---|---|---|
| | | Dry Weight (mg/ml) | Emulsifying Activity (units/ml) | Specific Activity (units/mg) |
| High Producers | | | | |
| BD4 | 2.40 | 0.74 | 239 | 323 |
| NS-1 | 1.69 | 2.60 | 235 | 90 |
| NS-4 | 2.57 | 0.97 | 178 | 184 |
| 1612 | 2.60 | 0.82 | 170 | 207 |
| NS-6 | 2.60 | 1.60 | 140 | 132 |
| RAG-1 | 2.56 | 0.90 | 115 | 128 |
| NS-5 | 2.51 | 0.76 | 101 | 132 |
| 1935 | 2.38 | 0.58 | 88 | 152 |
| Low Producers | | | | |
| NS-2 | 3.71 | 0.92 | 55 | 60 |

TABLE 4-continued
EXTRACELLULAR BIOEMULSIFIER PRODUCTION BY A. CALCOACETICUS STRAINS*

| Strain | Cell Yield Dry Weight (mg/ml) | Extracellular Dialysate** Dry Weight (mg/ml) | Emulsifying Activity (units/ml) | Specific Activity (units/mg) |
|---|---|---|---|---|
| NS-8 | 1.60 | 0.21 | 52 | 248 |
| 17906 | 1.18 | 0.34 | 48 | 141 |
| NS-7 | 1.47 | 1.96 | 40 | 20 |
| NS-9 | 1.33 | 0.33 | 36 | 109 |
| NS-3 | 1.61 | 0.66 | 32 | 48 |
| 17924 | 1.65 | 0.46 | 27 | 59 |
| HO1-N | 1.04 | 0.38 | 14 | 37 |

*Cultures were grown for 72 hours at 30° C. in EMS medium.
**The cell-free supernatant was dialyzed against distilled water before determination of dry weight and emulsifying activity on a hexadecane/2-methylnapthalene mixture.

The data shown in Table 4 indicate that on the basis of emulsifying activity, a rough division of the microbial strains into high and low bioemulsifier producers may be made. Generally, there was a correlation between cell yield and the production of emulsifying activity, but there were exceptions. Strains NS-1 produced relatively little cell mass but the highest amount of extracellular material with high emulsifying activity per unit volume of medium. In contrast, strain NS-2 achieved the higher cell mass but produced relatively low emulsifying activity.

The specific activities of the crude bioemulsifier preparations varied considerably. It is not clear whether this was due to the production of other extracellular polymers that have no emulsifying activity or to intrinsic differences in the specific activities of the various emulsifiers, or to materials such as proteins or polypeptides that may have bound to the bioemulsifiers and altered their emulsifying activities [See Section 5.4, below]. The extracellular dialysate of each strain was examined for carbohydrate and protein content (Section 5.3.1), however, and in all of the strains that produced high amounts of bioemulsifier, the weight ratio of extracellular carbohydrate to protein was greater than 2.5.

To determine the hydrocarbon specificities of the bioemulsifiers shown in Table 4, the polymers were tested on the hydrocarbons hexadecane, 2-ethylnaphthalene or on a 1:1 mixture of hexadecane/2-methylnaphthalene. The results are shown in Table 5.

TABLE 5
HYDROCARBON SPECIFICITIES OF THE BIOEMULSIFIERS

| Emulsifier Source* | Hexadecane/ 2-Methyl- naphthalene** | Hexadecane | 2-Ethyl- naphthalene |
|---|---|---|---|
| High Producers | | | |
| BD-4 | 239 | 0 | 31 |
| NS-1 | 235 | 86 | 10 |
| NS-4 | 178 | 0 | 17 |
| 1612 | 170 | 25 | 38 |
| NS-6 | 140 | 0 | 112 |
| RAG-1 | 115 | 83 | 16 |
| NS-5 | 101 | 83 | 12 |
| 1935 | 88 | 24 | 24 |
| Low Producers | | | |
| NS-2 | 55 | 0 | 28 |
| NS-8 | 52 | 0 | 0 |
| 17906 | 48 | 0 | 0 |
| NS-7 | 40 | 124 | 7 |
| NS-9 | 36 | 0 | 0 |
| NS-3 | 32 | 0 | 0 |
| 17924 | 27 | 0 | 0 |
| HO1-N | 14 | 0 | 0 |

*The dialyzed cell-free supernatant fluid described in Table 4 was used.
**Data are from TABLE 4.

As shown in Table 5, except for strain NS-7, the emulsifying activities were greater for the hexadecane/2-methylnaphthalene mixture than for hexadecane or 2-ethylnaphthalene alone. The emulsifying agents from strains NS-1, RAG-1, NS-5 and NS-7 emulsified hexadecane considerably better than 2-ethylnaphthalene. The emulsifiers of strains BD-4, NS-6 and NS-2, and to a lesser degree those of strains NS-4 and 1612, were more effective with the aromatic than with the aliphatic hydrocarbon.

5.4. EFFECT OF PROTEASE TREATMENT ON THE BIOEMULSIFIERS

As noted in Section 4.3, the bioemulsifiers produced by the *A. calcoaceticus* strains of this invention are likely to be complexed with proteins or polypeptides which may alter their emulsifying activity. To demonstrate this fact, some of the strains were grown in EMS medium containing 2 volume percent ethanol, as described in Section 5.3.3. Data related to cell production and to the characteristics of the culture media of the strains were then obtained as shown in Table 6. In addition, aliquots of the culture media were treated for 60 minutes at 50° C. with 500 ug/ml Maxatase (trade name for a *Bacillis subtilis* general protease marketed by Gist Brocades). After the protease treatment, the weights and the emulsifying activities of the treated bioemulsifiers were determined.

Bioemulsifier weight was determined by high pressure liquid chromatography (HPLC) in a Waters' I-300 molecular sieve column. The column was monitored at 205 nm, and the areas under the emergent peaks were integrated and compared with that of a highly purified emulsan sample. Any differences between the molar extinction coefficients for the bioemulsifiers and for the emulsan were assumed to be minor.

TABLE 6
EFFECT OF PROTEASE DIGESTION UPON BIOEMULSIFIER ACTIVITY*

| Strain | Cell Yield Dry Weight (g/L) | Extracellular Culture Medium Dry Weight (g/L)+ | Emulsifying Activity (O.D.$_{660}$) | Specific Activity (O.D.$_{660}$/ g polymer) | EACN** Specificty |
|---|---|---|---|---|---|
| PET-11 | 4.6 | 0.71 | 1.98 | 2.78 | 6 > 9 > 12 > 16 |

TABLE 6-continued
EFFECT OF PROTEASE DIGESTION UPON BIOEMULSIFIER ACTIVITY*

| | | Extracellular Culture Medium | | | |
|---|---|---|---|---|---|
| Strain | Cell Yield Dry Weight (g/L) | Dry Weight (g/L)+ | Emulsifying Activity (O.D.$_{660}$) | Specific Activity (O.D.$_{660}$/g polymer) | EACN** Specificty |
| NS-1 | 5.5 | (0.71) 2.94 | (1.50) 0.89 | (2.11) 0.31 | 6 > 16 > 9 > 12 |
| NS-4 | 4.3 | (2.44) 0.56 | (3.68) 0.27 | (1.51) 0.47 | 6 > 9 > 12 > 16 |
| NS-5 | 3.7 | (0.56) 2.34 | (0.12) 1.98 | (0.21) 0.85 | 6 > 9 > 12 > 16 |
| NS-6 | 4.1 | (2.13) 1.91 | (1.71) 2.10 | (0.84) 1.10 | 6 > 9 > 12 > 16 |
| NS-7 | 2.6 | (1.55) 1.78 | (2.10) 1.98 | (1.35) 1.11 | 9 > 6 > 12 > 16 |
| | | (1.06) | (2.52) | (2.38) | |

*Value shown in parentheses represent samples treated with a general protease from *Bacillus subtillis*.
**See legend to Table 3 for definition of EACN.
+Biopolymer weight was determined by HPLC, as described in the text.

As shown in Table 6, the effect of protease treatment on emulsifying activity was variable and unpredictable. For example, the activity of the PET-11 bioemulsifier decreased, while that of the NS-1 emulsifier strongly increased. Table 6 is also interesting because of its demonstration of the EACN specificity of the biopolymers. In general, protease treatment did not affect specificity, which tended to favor more aromatic hydrocarbons and to show progressively decreasing effectiveness as the aliphatic content of the mixtures increased. There were however, some anomalies. For example, the specificity of the bioemulsifier of NS-1 showed greater efficiency for emulsifying hexadecane than for more aromatic mixtures. Also, the bioemulsifier of NS-7 was more effective for EACN 9 than for EACN 6.

5.5. PREPARATION OF TECHNICAL GRADE BIOEMULSIFIERS

The bioemulsifiers produced by strains of *A. calcoaceticus* can be used as technical grade materials and can be prepared in either of two ways. Both methods of preparation involve enzyme treatment and drying but differ in the order in which these steps are performed. By one method, whole broth or centrifuged or filtered (approximately 85-100% cell-free) fermentation broth containing bioemulsifiers resulting from a fermentation of a strain of *Acinetobacter calcoaceticus* is dried and the resulting material is treated in the following manner prior to use. A suspension of the material, so-called technical grade biopolymer, is prepared in water or in a salt solution. The temperature is adjusted to the appropriate range for the protease used. The pH of the suspension is adjusted if necessary by adding acid or base.

A protease such as NOVO Industries' 1.5M Alcalase or trypsin is added at an appropriate level (typically 1 to 10 parts protease to 2,000 parts technical grade dry bioemulsifier). The mixture is then incubated at the appropriate temperature while being stirred for about ½ to about 3 hours. Reactions are run to completion as judged by the absence of visible precipitable material following centrifugation of the reaction mixture or as indicated by stabilized pH. If desired, the pH may be controlled during digestion by base addition. After completion of the enzyme treatment, the temperature of the reaction mixtures may be raised to approximately 70° to 100° C. to denature and inactivate the protease.

The solutions are cooled to a desired temperature and a suitable preservative may be added.

By another method, enzyme treatment of the bioemulsifier is performed prior to drying. Drying can be by freeze drying, drum drying or spray drying, depending upon the application or the available equipment. Fermentation broth containing bioemulsifier resulting from a fermentation of a strain of *Acinetobacter calcoaceticus* is used as a whole broth or after removal of 85-100% of the cells as described above. To the whole or substantially cell-free broth, protease is added (as previously described). The protease reaction is run to completion as described above. The protease-treated broth is then evaporated or ultrafiltered to a desired concentration (typically 5 to 20% total solid content). The slurry can be dried, and the material resulting from this method is also referred to as technical grade bioemulsifiers.

In one embodiment of the invention, centrifuged (approximately 90% cell-free) fermentation broth containing biomusifiers resulting from a fermentation of a strain of *Acinetobacter calcoaceticus* in ethanol medium was drum-dried. A 10% by weight suspension of the material was prepared in deionized water and heated to 50°-60° C. while continuously stirring. The pH of the suspension was adjusted to pH 8.5 by adding 50% by weight sodium hydroxide (diluted if necessary). Protease (NOVO Industries, 1.5M Alcalase) was added at a level of 1 part protease:500 parts solid bioemulsifier. The mixture was allowed to remain at 50°-60° C. while being stirred for about three hours.

After completion of the enzyme treatment, the reaction mixture was raised to approximately 70° C. to denature and inactivate the protease. The solution was cooled to room temperature and, Cosan PMA-30 (Cosan Corporation), a preservative, was added at a level of 1 part Cosan:500 parts bioemulsifier solution.

In another embodiment, fermentation broth containing bioemulsifier resulting from a fermentation of a strain of *A. calcoaceticus* in ethanol medium was centrifuged to remove approximately 90% of the bacterial cells. Protease was added as described for the first embodiment in a ratio of 1 gram protease:500 grams of technical grade bioemulsifier.

The protease reaction was run to completion as described above, and the protease-treated centrifuged broth was evaporated to a 10% (w/v) slurry of bioemulsifier. The slurry was spray dried when solid material was desired.

5.6. Additional Preparations of *Acinetobacter calcoaceticus* Bioemulsifiers Fermentations of *Acinetobacter calcoaceticus* can be run on ethanol or on other carbon sources as described in U.S. Pat. No. 4,395,354. The following fractions of the resulting broth can be used advantageously: whole broth, supernatants, cells, enzyme-treated whole broth, enzyme-treated supernatants, enzyme-treated cells (where the enzyme treatment was as described for the second method in Section 5.5.), homogenized cells, boiled cells, and so-called "purified bioemulsifier." Purified bioemulsifier is prepared by microporous filtration of whole broth through 0.2–0.5 micron filters or by centrifugation to remove cells and other particulates, followed by optional enzyme treatment (described above) and ultrafiltration. The foregoing preparations can be used in liquid or wet form. The purified bioemulsifier samples can be further dialyzed or ultrafiltered against ammonium bicarbonate or other salts or chaotropic agents and dried prior to use in surfactant packages. The bioemulsifiers may be solvent extracted to remove non-covalently bound lipids.

6. DEPOSITS OF MICROORGANISMS

The NS-1, -4, -5, -6 and -7 emulsifier-producing bacterial strains have been deposited with the Agricultural Research Culture Collection (NRRL), Peoria, Illinois, and have been assigned accession numbers NRRL B-15847, B-15848, B-15849, B-15860 and B-15850, respectively. Cultures of these deposited microorganisms will be made available to the public upon the grant of a patent based upon the present application. The invention described and claimed herein, however, is not to be limited in scope by the strains of microorganisms deposited. The deposited embodiments are intended to be only examples of one aspect of the invention, and any equivalent *Acinebacter calcoaceticus* strains which produce functionally equivalent bioemulsifiers are within the scope of the invention.

What is claimed is:

1. A substantially cell-free medium from a bacterial cell culture in which *Acinetobacter calcoaceticus* NRRL B-15847 has been grown, characterized by nondialyzable emulsifying activity for at least one hydrocarbon, comprising medium from a bacterial cell culture in which *Acinetobacter calcoaceticus* strain NRRL B-15847 has been grown and from which the bacterial cells have been substantially removed.

2. The substantially cell-free medium of claim 1 in which the hydrocarbon is an aromatic or aliphatic compound, or a mixture thereof.

3. A substantially cell-free medium from a bacterial cell culture in which *Acinetobacter calcoaceticus* NRRL B-15848 has been grown, characterized by nondialyzable emulsifying activity for at least one hydrocarbon, comprising medium from a bacterial cell culture in which *Acinetobacter calcoaceticus* strain NRRL B-15848 has been grown and from which the bacterial cells have been substantially removed.

4. A substantially cell-free medium from a bacterial cell culture in which *Acinetobacter calcoaceticus* NRRL B-15849 has been grown, characterized by nondialyzable emulsifying activity for at least one hydrocarbon, comprising medium from a bacterial cell culture in which *Acinetobacter calcoaceticus* strain NRRL B-15849 has been grown and from which the bacterial cells have been substantially removed.

5. A substantially cell-free medium from a bacterial cell culture in which *Acinetobacter calcoaceticus* NRRL B-15850 has been grown, characterized by nondialyzable emulsifying activity for at least one hydrocarbon, comprising medium from a bacterial cell culture in which *Acinetobacter calcoaceticus* strain NRRL B-15850 has been grown and from which the bacterial cells have been substantially removed.

6. A substantially cell-free medium from a bacterial cell culture in which *Acinetobacter calcoaceticus* NRRL B-15860 has been grown, characterized by nondialyzable emulsifying activity for at least one hydrocarbon, comprising medium from a bacterial cell culture in which *Acinetobacter calcoaceticus* strain NRRL B-15860 has been grown and from which the bacterial cells have been substantially removed.

7. A partially-purified bioemulsifier preparation from a substantially cell-free medium of a bacterial cell culture in which *Acinetobacter calcoaceticus* strain NRRL B-15847 has been grown, characterized by nondialyzable emulsifying activity for at least one hydrocarbon, comprising medium from a bacterial cell culture in which *Acinetobacter calcoaceticus* strain NRRL B-15847 has been grown, which medium has been dialyzed following removal of the bacterial cells.

8. The partially-purified bioemulsifier preparation of claim 7 in which the preparation is characterized by a Specific Emulsification Activity of about 90 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

9. The partially-purified bioemulsifier preparation of claim 7 in which the hydrocarbon is an aromatic or aliphatic compound, or a mixture thereof.

10. A partially-purified bioemulsifier preparation from a substantially cell-free medium of a bacterial cell culture in which *Acinetobacter calcoaceticus* strain NRRL B-15848 has been grown, characterized by nondialyzable emulsifying activity for at least one hydrocarbon, comprising medium from a bacterial cell culture in which *Acinetobacter calcoaceticus* strain NRRL B-15848 has been grown, which medium has been dialyzed following removal of the bacterial cells.

11. The partially-purified bioemulsifier preparation of claim 10 in which the preparation is characterized by a Specific Emulsification Activity of about 184 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

12. A partially-purified bioemulsifier preparation from a substantially cell-free medium of a bacterial cell culture in which *Acinetobacter calcoaceticus* strain NRRL B-15849 has been grown, characterized by nondialyzable emulsifying activity for at least one hydrocarbon, comprising medium from a bacterial cell culture in which *Acinetobacter calcoaceticus* strain NRRL B-15849 has been grown, which medium has been dialyzed following removal of the bacterial cells.

13. The partially-purified bioemulsifier preparation of claim 12 in which the preparation is characterized by a Specific Emulsification Activity of about 132 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

14. A partially-purified bioemulsifier preparation from a substantially cell-free medium of a bacterial cell culture in which *Acinetobacter calcoaceticus* strain NRRL B-15850 has been grown, characterized by non-dialyzable emulsifying activity for at least one hydrocarbon, comprising medium from a bacterial cell culture in which *Acinetobacter calcoaceticus* strain NRRL B-15850 has been grown, which medium has been dialyzed following removal of the bacterial cells.

15. The partially-purified bioemulsifier preparation of claim 14 in which the preparation is characterized by a Specific Emulsification Activity of about 20 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

16. A partially-purified bioemulsifier preparation from a substantially cell-free medium of a bacterial cell culture in which *Acinetobacter calcoaceticus* strain NRRL B-15860 has been grown, characterized by non-dialyzable emulsifying activity for at least one hydrocarbon, comprising medium from a bacterial cell culture in which *Acinetobacter calcoaceticus* strain NRRL B-15860 has been grown, which medium has been dialyzed following removal of the bacterial cells.

17. The partially-purified bioemulsifier preparation of claim 16 in which the preparation is characterized by a Specific Emulsification Activity of about 132 units per milligram of higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

18. A substantially pure culture of *Acinetobacter calcoaceticus* NRRL B-15847 or a mutant thereof.

19. A substantially pure culture of *Acinetobacter calcoaceticus* NRRL B-15848 or a mutant thereof.

20. A substantially pure culture of *Acinetobacter calcoaceticus* NRRL B-15849 or a mutant thereof.

21. A substantially pure culture of *Acinetobacter calcoaceticus* NRRL B-15850 or a mutant thereof.

22. A substantially pure culture of *Acinetobacter calcoaceticus* NRRL B-15860 or a mutant thereof.

* * * * *